(12) United States Patent
Flohr

(10) Patent No.: US 7,616,730 B2
(45) Date of Patent: Nov. 10, 2009

(54) METHOD AND CT SYSTEM FOR CARRYING OUT A CARDIO-CT EXAMINATION OF A PATIENT

(75) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/987,473

(22) Filed: Nov. 30, 2007

(65) Prior Publication Data

US 2008/0144765 A1    Jun. 19, 2008

(30) Foreign Application Priority Data

Dec. 1, 2006   (DE) .................. 10 2006 056 884

(51) Int. Cl.
*G01N 23/00*   (2006.01)

(52) U.S. Cl. .................. 378/8; 378/9; 378/95; 378/901

(58) Field of Classification Search ...... 378/4, 378/8, 9, 91, 95, 114–116, 901
See application file for complete search history.

(56) References Cited

U.S. PATENT DOCUMENTS 6,421,412 B1   7/2002   Hsieh et al.
7,187,746 B2 *  3/2007   Sakaguchi et al. ............. 378/8
2007/0183561 A1 *  8/2007   Bruder .......................... 378/8

OTHER PUBLICATIONS

German Office Action.

\* cited by examiner

*Primary Examiner*—Jurie Yun
(74) *Attorney, Agent, or Firm*—Harness, Dickey & Pierce, P.L.C.

(57) ABSTRACT

A method and a CT system are disclosed for carrying out a cardio-CT examination of a patient. The patient first is scanned using a first X-ray spectrum by way of at least two X-ray tubes at a first relative position, until the measurement data has been gathered from a determined heart phase for parallel projections over a range of in total at least 180° of projection angles. The patient is then scanned, without changing the position of the gantry, at the first relative position by way of at least two X-ray tubes using at least one second X-ray spectrum, until the measurement data has been gathered from a determined heart phase for parallel projections over a range of at least 180° of projection angles, upon which the next relative position between the patient and the gantry is moved to.

23 Claims, 4 Drawing Sheets

METHOD AND CT SYSTEM FOR CARRYING
OUT A CARDIO-CT EXAMINATION OF A
PATIENT

PRIORITY STATEMENT

The present application hereby claims priority under 35 U.S.C. §119 on German patent application number DE 10 2006 056 884.2 filed Dec. 1, 2006, the entire contents of which is hereby incorporated herein by reference.

FIELD

Embodiments of the invention generally relate to a method and/or a CT system for carrying out a cardio-CT examination of a patient. In at least one embodiment, this can be done, for example, using a CT system having at least two X-ray tubes which are arranged at offset angles with respect to one another on a gantry, wherein a current EKG signal of the patient is recorded, the patient and the gantry are moved sequentially relative to one another in the system axis direction, while the at least two X-ray tubes, which are arranged at offset angles with respect to one another, are moved on a circular path around the patient for scanning and absorption data of the patient is measured, and computed-tomography representations of the patient are then produced using selected absorption data.

BACKGROUND

A method and a CT system are generally known.
Furthermore, it is also generally known for patients to be scanned using CT systems with X-ray tubes which are arranged at offset angles with respect to one another and using different energy spectra, so as to make it possible to distinguish better between the scanned tissue and the deposits which may be present in that tissue.

SUMMARY

In at least one embodiment of the invention, a method and/or a CT system are disclosed for carrying out a cardio-CT examination, in which on the one hand the scan is carried out using at least two different energy spectra and, on the other hand, it is also possible to exploit the advantage of the better time resolution of X-ray tubes which are arranged at offset angles with respect to one another.

The inventor has found the following:
When carrying out CT examinations, it is sufficient when using a parallel geometry to use a projection angle range of 180°—that is to say a half-revolution data interval—in order to reconstruct the realistic slice images. When recording data using a fan geometry, a fan data record of 180° plus the fan angle of the detector is necessary in order to obtain 180° parallel data for each image point within the measurement field. At the rotation center, 180° of fan data is sufficient to obtain 180° of parallel data.

In a CT system with two X-ray sources which are arranged with an angle offset of 90° this half-revolution data record can be subdivided using parallel geometry into two quarter-revolution data records which are recorded by the two measurement systems at the same time with a 90° offset between them. These two quarter-revolution data records can be joined to one another with the aid of a smoothing transfer function, with the smoothing ensuring that artifact streaks resulting from possible inconsistencies between the two start and end projections are avoided. This results in a half-revolution interval, which is sufficient for image reconstruction, using parallel geometry from data which both measurement systems have recorded at the same time in the time interval of a quarter of the gantry rotation time. Unfortunately, this technique does not allow dual-energy applications, unless the time resolution is dispensed with. If the aim is therefore to calculate an 80 kV image and a 140 kV image at the same time from the data from one heart period, each image must be calculated separately from a half-revolution data record of the respective measurement system, and therefore has a time resolution of only half the gantry rotation time.

The inventor has therefore proposed, in at least one embodiment, a novel method for cardio-CT image production using a plurality of energy spectra in which, once again using a plurality of energy spectra, the time resolution of the CT system is improved corresponding to the number of radiation sources that are used. For this purpose, the patient couch can first of all be moved sequentially from a z position, on the basis of EKG triggering, with a sequential partial revolution scan first of all being recorded at each z position, at the desired time interval from the last R peak of the EKG, using a tube voltage of 120 kVp or 140 kVp, for example, for both measurement systems in a dual-source CT system, corresponding to the requirements for a CT-angiographic examination of the coronary arteries. The time resolution of a scan such as this when using a dual-source CT is in each case one quarter of the revolution time.

After this first data recording, the couch is not moved any further from the z position predefined by the user and, instead, this is followed by a further sequential partial revolution scan using, for example, 80 kVp for both measurement systems. The time from one heart period to the next is sufficient to switch both the tube voltage and the tube current so that, if desired, approximately equal doses can be achieved for the two scans, which may be particularly advantageous for dual-energy evaluation. The further movement to the next z position does not take place until after the 80 kVp recording has been made, and this is followed by a recording using 120 kVp or 140 kVp at the new z position. This process can be continued until the predetermined region of the patient has been scanned completely.

This allows the entire heart to be mapped CT-angiographically with the best possible time resolution within the same examination and using the same contrast agent bolus, and it is also possible to obtain dual-energy information, for example in order to assess the myocardium or coronary plaque, at individual predefined points.

In a corresponding manner to this idea of at least one embodiment of the invention as described above, the inventor has proposed an improvement to the known method for carrying out a cardio-CT examination of a patient using a CT system with at least two X-ray tubes which are arranged at offset angles with respect to one another on a gantry, having the following method steps:

a current EKG signal is taken from the patient,
the patient and the gantry are moved sequentially relative to one another in the system axis direction, while
the at least two X-ray tubes which are arranged at offset angles with respect to one another are moved on a circular path around the patient for scanning, and absorption data of the patient is measured, and
computed-tomography representations of the patient are produced using selected absorption data.

According to an embodiment of the invention, this method which is known per se is now complemented by carrying out the following method steps as well:

the patient is scanned using two different X-ray spectra at at least two relative positions, which are driven to sequentially, between the patient and the gantry, wherein the patient is first of all scanned using a first identical X-ray spectrum by way of at least two X-ray tubes at a first relative position, until the measurement data has been gathered for parallel projections over a range of in total at least 180° of projection angles from a predetermined heart phase, without any change in the position of the gantry, the patient is scanned at the first relative position by way of at least two X-ray tubes using at least one second X-ray spectrum, until the measurement data has been gathered for parallel projections over a range of at least 180° of projection angles from a predetermined heart phase, and the next relative position between the patient and the gantry is then moved to.

In this embodiment of the method, no spiral scan is therefore carried out but, instead, the gantry is moved relative to the patient, or relative to the patient couch, sequentially in steps which are triggered by the heartbeat of the patient, in the z direction or the system axis direction, with the different energy spectra each being switched for a circular scan over at least 180° successively at each relative position.

The method described above can be used not only with a CT system with three X-ray tubes which are arranged with angular offsets of 120°, but also in another embodiment with a CT system with two X-ray tubes which are arranged with an angular offset of 90°.

The different radiation energy spectra may be achieved, for example, by variation of the acceleration voltage or by the use of different radiation filters, or else by a combination of both measures.

It is also advantageous for the tube current to be matched during the variation of the energy spectrum such that the applied dose rate remains the same. This makes it possible to ensure that the dose load to the patient is kept as low as possible, irrespective of the energy spectrum that is used.

The relative movement between the patient and the gantry in the system axis direction can be carried out either by movement of a patient couch on which the patient is located in the system axis direction or by movement of the gantry with respect to a stationary patient couch.

In one particular embodiment of the method, the inventor proposes that the change in the energy spectra and the relative movement between the patient and the gantry triggered by the recorded EKG signals take place in that, first of all, in a first heart period during the rest phase, projections over an angle range of at least 180° are produced and recorded using a first energy spectrum overall by way of at least two beam sources and a respectively associated detector, and then, in a second, subsequent heart period during the rest phase, projections over an angle range of at least 180° are produced and recorded using a second energy spectrum overall by way of at least two beam sources and a respectively associated detector, and the relative movement between the gantry and the patient then takes place directly in the system axis direction, such that a scan can be carried out once again with the first energy spectrum even in the next heart period. The method then starts again and can be carried out until a predetermined heart region or the entire heart region has been scanned.

Alternatively, it is also possible that, after the relative movement, in a third heart period during the rest phase, projections over an angle range of at least 180° are produced and recorded using the second energy spectrum overall by way of at least two beam sources and a respectively associated detector, and in a fourth, subsequent heart period during the rest phase, projections over an angle range of at least 180° are produced and recorded using the first energy spectrum overall by way of at least two beam sources and a respectively associated detector, and the relative movement between the gantry and the patient takes place in the system axis direction, with the method then being started again.

According to a further variant of an embodiment of the method, the inventor proposes that the change in the energy spectra and the relative movement between the patient and the gantry are triggered by the recorded EKG signals, in that:

in a first heart period during the rest phase, projections over an angle range of at least 180° are produced and recorded using a first energy spectrum overall by way of at least two beam sources and a respectively associated detector, in a second, subsequent heart period during the rest phase, projections over an angle range of at least 180° are produced and recorded using a second energy spectrum overall by way of at least two beam sources and a respectively associated detector, and the relative movement between the gantry and the patient in the system axis direction takes place in a third, subsequent heart period.

This most recently described method makes it possible to carry out the sequential method even when the heart rate frequency is relatively high. This results in a greater time interval for the relative movement between the patient and the gantry, as a result of which there is also a sufficiently long time interval in which the body of the patient comes to rest after the acceleration and braking phase, so that the CT scan is not disturbed by the patient "waking up" as a result of the severe acceleration of the patient couch.

On the one hand, it is now possible to continue using the method described above, or else, in this case, it is possible to use a procedure relating to the change in the energy spectra such that:

in a fourth heart period during the rest phase, projections over an angle range of at least 180° are produced and recorded using the second energy spectrum overall by way of at least two beam sources and a respectively associated detector, in a fifth, subsequent heart period during the rest phase, projections over an angle range of at least 180° are produced and recorded using the first energy spectrum overall by way of at least two beam sources and a respectively associated detector, and the relative movement between the gantry and the patient in the system axis direction again takes place in a sixth, subsequent heart period.

The most recently described method has the advantage that the number of changes between the individual energy spectra is somewhat less since, in this case, the same energy spectrum is in each case retained over two heart periods in which scans are carried out.

It is particularly advantageous for no dose power to be emitted to the patient during the relative movement between the patient and the gantry in the system axis direction, that is to say in the time in which no measurement data is being recorded. This is particularly advantageous for that variant of the method in which the relative movement between the patient and the gantry is carried out in a separate heart period.

Particularly when using CT systems having three X-ray sources which are arranged with angular offsets of 120°, it may be particularly advantageous for complementary beams to be taken into account as well for gathering projection data over a projection angle range of at least 180°.

While in the case of a CT system with two radiation sources which are arranged with an angular offset of 90° a gantry rotation through just 90° plus the fan angle is sufficient to achieve a complete record of projections over 180°, it is sufficient with a system having three radiation sources which are arranged with angular offsets of 120° to just rotate the gantry through 60° plus the fan angle in order to obtain a complete projection data record although, in this case, it is absolutely essential to also take account of complementary beams, that is to say beams in the opposite direction, in the evaluation process.

It is also advantageous for the method described above to be carried out only over a subarea of the heart, with the rest of the scan of the patient being carried out using a single energy spectrum. In addition, it is also particularly advantageous to use at least two energy spectra whose energy ranges do not overlap.

In a corresponding manner to the method according to an embodiment of the invention as described above, the inventor also proposes a CT system for production of computed-tomography representations of a patient with a beating heart, having at least two radiation sources which are arranged at offset angles with respect to one another, rotate about a system axis and pass radiation through the patient, with the absorption of the radiation being measured, and a control and computation unit having a memory, which contains program code, which evaluates the recorded measurement data during operation and reconstructs the computed-tomography representations, according to an embodiment of the invention with program code being stored in the memory and carrying out the method steps according to the above-described method variants.

BRIEF DESCRIPTION OF THE DRAWINGS

The invention will be described in more detail in the following text with the aid of the figures and with reference to the example embodiments, with the only features that are described being those which are necessary for understanding the embodiments of the invention. The following reference symbols are used in this case: 1: CT system, 2: first X-ray tube, 3: housing of the first detector; 4: second X-ray tube; 5: housing of the second detector; 6: gantry housing; 7: patient; 8: patient couch; 9: system axis; 10: control and computation unit; 11: program memory; 12: contrast agent pump; 13: EKG output cable; 14: control and data cable for gantry and patient couch; 15: control cable for contrast agent pump; 16: EKG output line; 17: R peak; 18: profile of the acceleration voltage of the X-ray tubes; 19: profile of the relative positions between the gantry and the patient; 20: profile of the tube current; 21: duration of a heart period; 22.1: first radiation filter, 22.2: second radiation filter; 23: heart; $D_i$: i-th detector; $F_i$: i-th focus; $I_R$: tube current; $Prg_1$-$Prg_n$: program code; $R_i$: time position of the R peak; $S_{1,i}$: beam fan; $S_{2,i}$: beam fan, t: time; U: tube voltage; $U_i$: tube voltage for the i-th energy spectrum; z: z axis.

In the figures, in detail.

DETAILED DESCRIPTION OF THE EXAMPLE EMBODIMENTS

Figure 1:
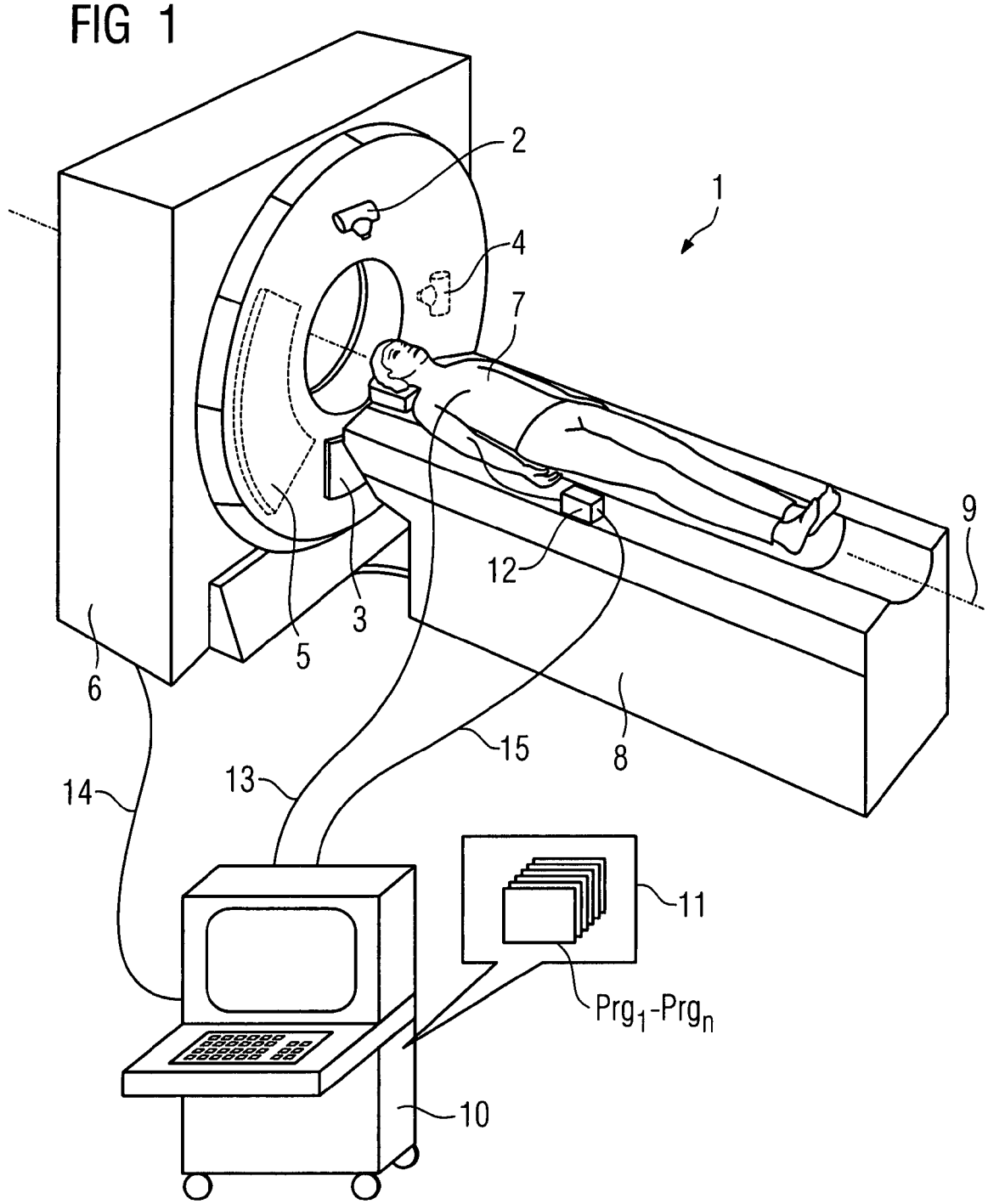
FIG. 1 shows a perspective 3D illustration of a CT system according to an embodiment of the invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a schematic 3D illustration of a CT system 1 according to the invention with two tube detector systems 2, 3 and 4, 5, which are offset through an angle of 90° and are arranged on a gantry in a gantry housing 6. A patient 7 is located on a movable patient couch 8 and is provided with contrast agent via an automatic contrast agent pump 12 at a predetermined time, at which the actual cardio-scan begins, so as to allow the vessels to be displayed better.

According to an embodiment of the invention, the gantry and the X-ray tubes 2 and 4 arranged on it, including the forward movement of the patient couch 8 are controlled via the control and data line 14 by a control and computation unit 10 in whose memory 11 computer programs $Prg_1$ to $Prg_n$ are located, such that a sequential scan is carried out at least in a predetermined area of the patient, with the two X-ray tubes 2 and 4 that are shown here each emitting an identical X-ray spectrum during a first heart period, in particular during the rest phase of the first heart period, which spectra are recorded by the opposite detectors in the detector housings 3 and 5, while the patient is himself or herself located in the measurement field of the two X-ray tubes 2, 4, without any forward movement. At the end of the rest phase of the first heart period, the acceleration voltage for the two X-ray tubes is switched such that, at the start of the rest phase of the subsequent second heart period, these two X-ray tubes emit a second X-ray spectrum, which is used to scan the patient's heart during the second rest phase with the aid of the two X-ray tubes 2, 4. This process is triggered via the output line from an EKG of the patient 7 via the EKG line 13, in which case, the R peak in the EKG can generally be used as the trigger pulse.

After the end of the two successive heart periods, the patient couch 8 may be moved forwards between the end of the rest phase of the second heart period and the start of the rest phase of the third heart period, such that the patient 7 is positioned in a new relative position with respect to the gantry. However, it is also possible to use the time of an entire intermediate third heart period for this forward movement. This procedure can be continued until either a specific area of the heart or the entire heart has been completely scanned with the aid of the two energy spectra. The actual control or the procedure for this method is controlled by the programs $Prg_1$ to $Prg_n$ contained in the control and computation unit 10.

Figure 2:
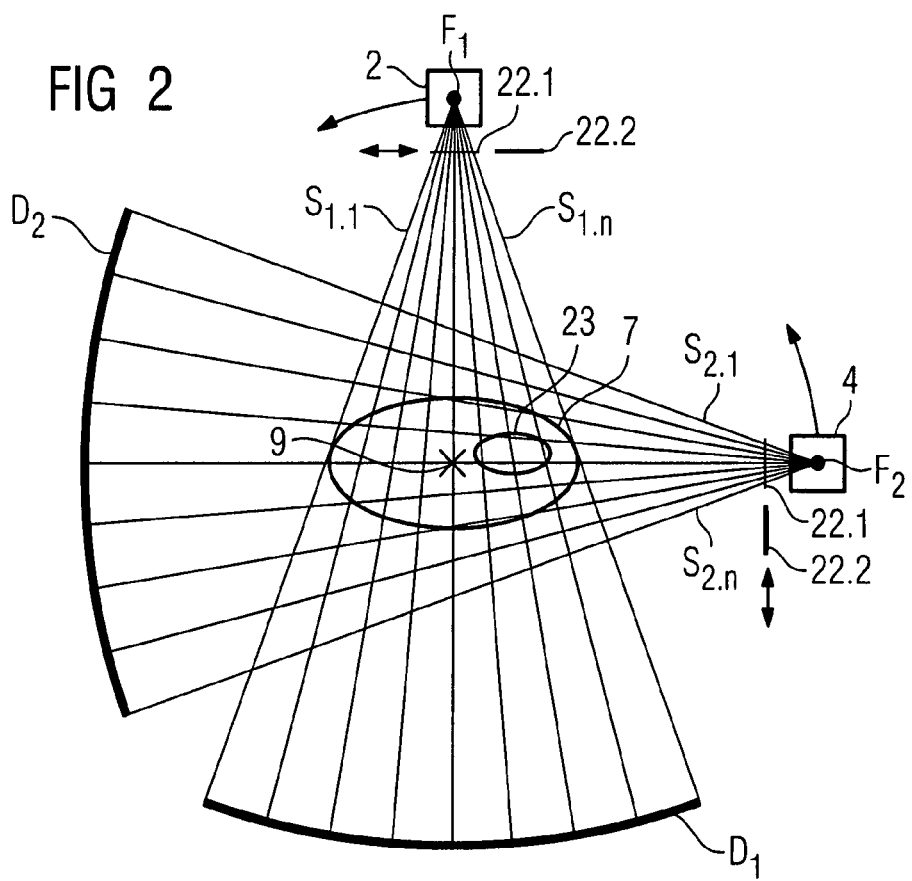
FIG. 2 shows a cross section through a schematically illustrated CT system with two X-ray tubes offset through 90°.
Figure 3:
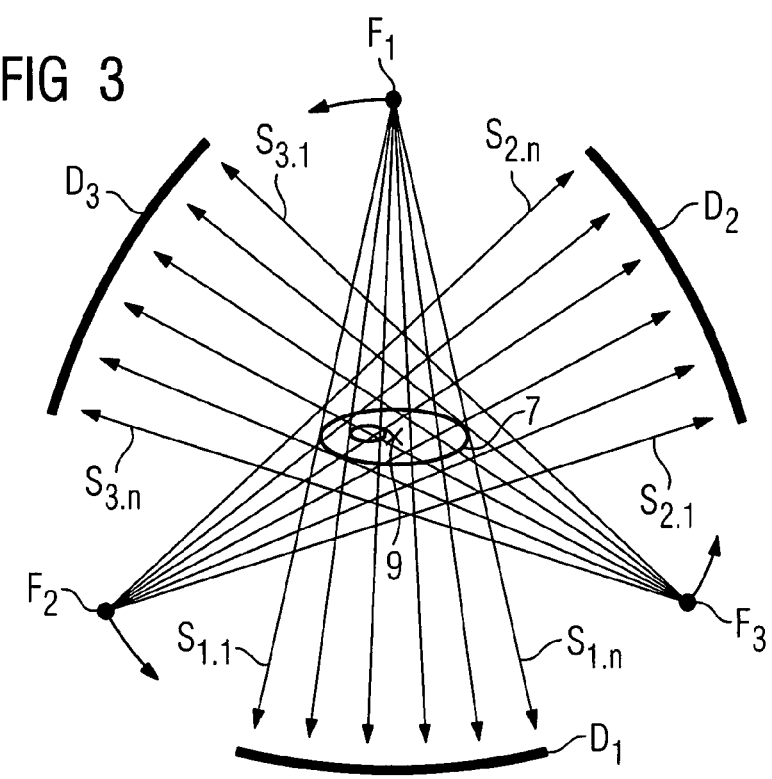
FIG. 3 shows a cross section through a schematic illustration CT system with three X-ray tubes offset through 120°.

FIGS. 2 and 3 show two schematic cross sections through CT systems on the plane of the gantry.

FIG. 2 shows a CT system with two X-ray tubes 2 and 4, including the focuses $F_1$ and $F_2$ arranged in them.

The X-ray tubes 2 and 4 are arranged on one plane and offset through an angle of 90° such that their beam fans $S_{1,1}$ to $S_{1,n}$ and $S_{2,1}$ to $S_{2,n}$ likewise extend with an angle offset at 90° from the respective focus $F_1$ or $F_2$ to the opposite respective detector $D_1$ or $D_2$. The arrangement shown here indicates that it is sufficient to rotate the gantry around the patient 7 who is located in the measurement field, in particular including the heart 23 arranged in this patient as well, through a rotation of 90° plus the fan angle for scanning purposes, so as to allow a complete record of projections to be recorded.

A corresponding situation applies to the CT system illustrated in FIG. 3. In this case, three focuses $F_1$, $F_2$ and $F_3$ are illustrated, which are arranged offset through 120° and are arranged opposite the detectors $D_1$, $D_2$ and $D_3$. With a CT system such as this, it is sufficient to rotate the system through 60° plus the fan angle of the beam fans that are used in order to obtain a complete record of projections for reconstruction of slice images. However, with the illustrated arrangement, it is necessary to also use beams aligned in a complementary form in order to gather parallel projections. Since, ignoring the problem of different beam hardening, two beams in opposite directions which travel over the same distance are subject to identical absorption, this can also be used to a first approximation.

Figure 4:
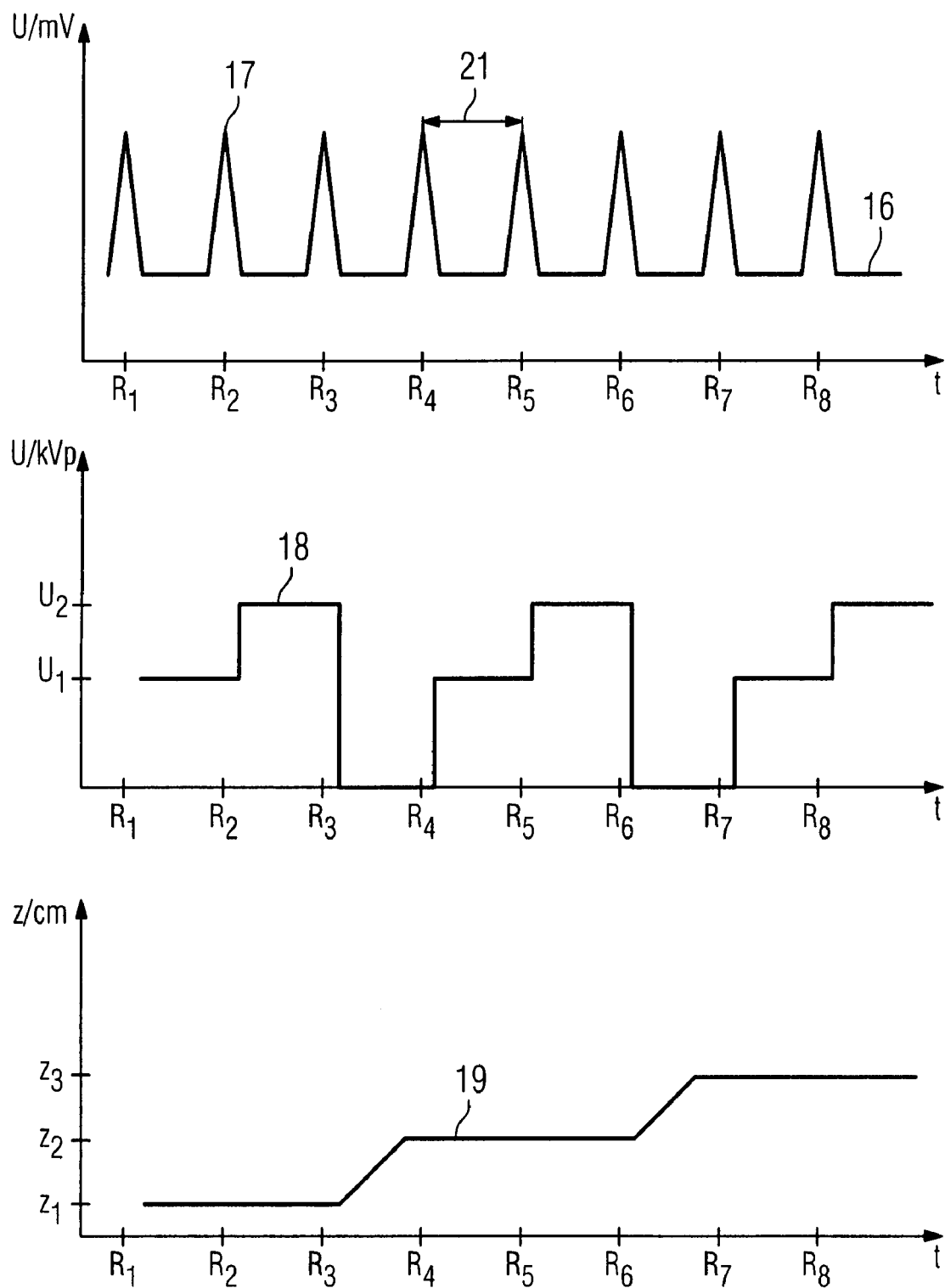
FIG. 4 shows a first variant of the timing between voltage switching for the tube voltage and the forward movement of the patient couch.
Figure 5:
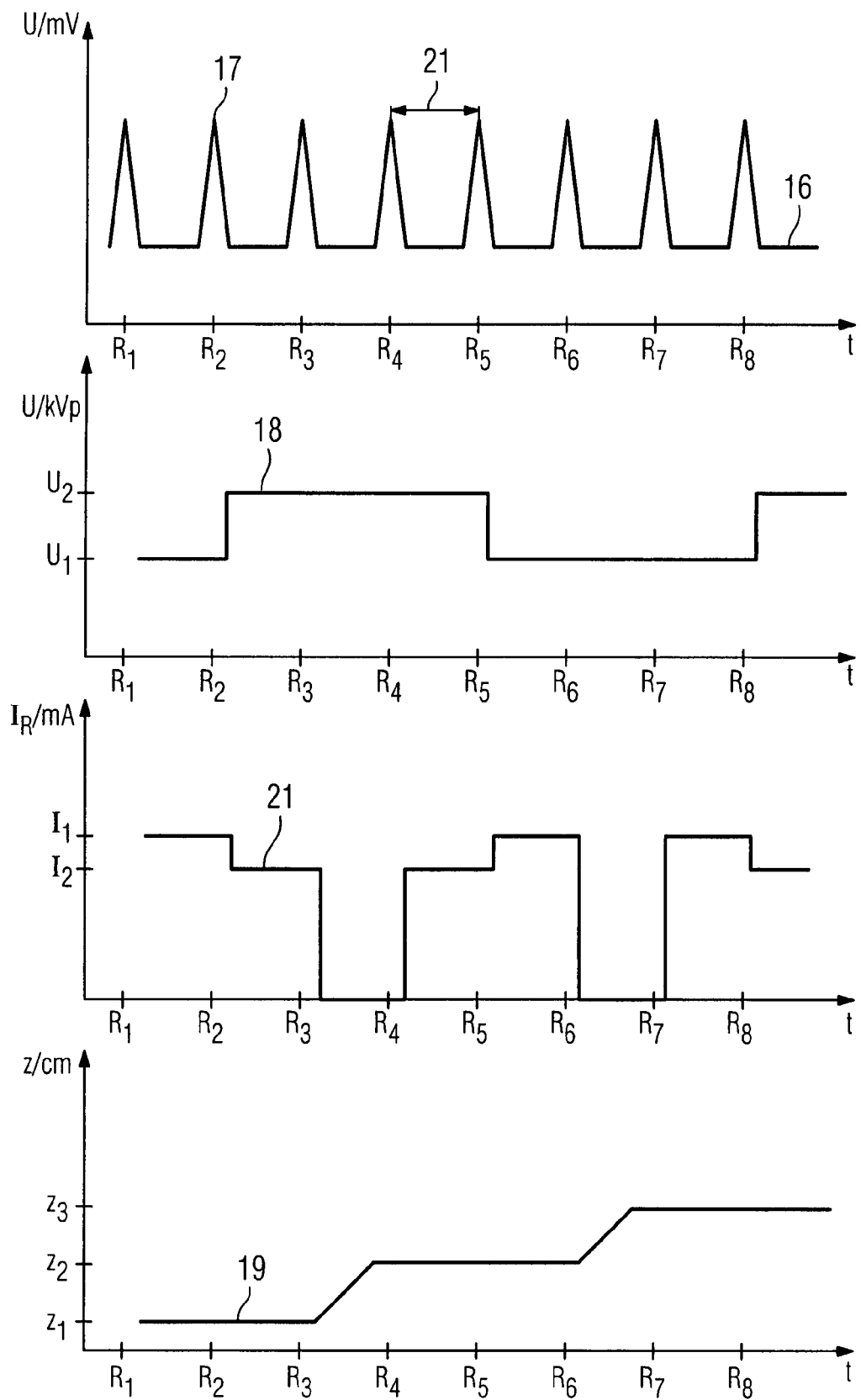
FIG. 5 shows a second variant of the timing of the tube voltage, of the tube current and of the forward movement in relation to the EKG of the patient.

Two variants of the timing according to an embodiment of the invention for the CT system with regard to the control of the tube voltage are illustrated in FIGS. 4 and 5.

In the first, upper diagram, FIG. 4 shows the schematic profile of an EKG signal 16 with the typical R peak 17, which are preferably used to trigger the switching of the tube voltage and the step-by-step forward movement of the patient couch. In this case, the EKG signal 16 is plotted over the time axis t and is illustrated in arbitrary millivolt units of the voltage potential U.

The duration of one heart period 21 is shown by way of example, with the time positions of the R peak $R_i$ also being shown on the time axis.

Using the same time axis, the voltage profile of the tube voltage U is plotted in arbitrary units in kVp in the central diagram in FIG. 4. At the same time, the lower graph shows the relative movement between the gantry and the patient in cm, plotted over the same time axis. As can be seen from these graphs, a voltage $U_1$ is first of all applied to the X-ray tubes in the first interval between $R_1$ and $R_2$.

After the end of the first interval, the voltage of the X-ray tubes is increased to $U_2$ while there is no relative movement between the gantry and the patient, at the same time. After the end of the second interval, at $R_3$, the voltage potential is reduced to 0, corresponding to the profile 18, so that the dose power value is likewise 0, while the relative position between the gantry and the patient is moved from $z_1$ to $z_2$, corresponding to the profile of the relative positions 19. The control process is in this case carried out such that the end position is preferably reached sufficiently before the start of the next rest phase, so that vibration no longer affects the patient or the gantry during the subsequent rest phase in the next heart period between $R_4$ and $R_5$, and the next scan can now be carried out, using the voltage $U_1$.

After the time, $R_5$, this is once again followed by the voltage being increased to $U_2$, so that the next scan can be carried out during the next heart period, between $R_5$ and $R_6$, using the second voltage $U_2$. This method is continued until all of the heart region has been scanned, with the distance between the z positions $z_1$ and $z_2$ preferably corresponding at most to the width of the detector in the z direction, so that the scanned region is scanned without any gaps.

FIG. 5 once again shows a similar illustration to that in FIG. 4, but additionally showing the profile 20 of the tube current IR/mA. As in FIG. 4, the scan in this case as well starts with the tube voltage $U_1$ over the time period of the first period $R_1$ to $R_2$. Without any change in the relative position between the gantry and the patient, the tube voltage is then increased to the magnitude $U_2$, which is used to carry out the scan in the second heart period $R_2$ to $R_3$.

In the third heart period, the acceleration voltage $U_2$ of the X-ray tube is maintained, but the tube current is reduced to 0 after the time $R_2$ so that no dose power is emitted and the patient couch is moved forwards during this time thus resulting in a change in the relative position between the gantry and the patient from the position $z_1$ to the position $z_2$. The tube current is then once again raised to the level $I_2$, and the period between $R_4$ and $R_5$ is carried out using the tube voltage $U_2$ and the tube current $I_2$. After this, the tube voltage is reduced to $U_1$, while the tube current is at the same time raised to the level $I_1$, etc. In this case, it should be noted that the tube voltage and the tube currents are now controlled in opposite senses so that the total dose power which is emitted from the X-ray tubes is identical at the different tube voltages that are used.

It should also be noted that it is within the scope of embodiments of the invention for the positional change between the individual relative positions between the gantry and the patient to be carried out between the rest phases of two mutually adjacent heart periods. This ensures that the scan is carried out quickly although high acceleration values can occur in the positioning phase if the heart rates of the patients being examined are relatively high, and these may possibly have a negative effect on the image quality.

It is self-evident that the features of the embodiments of invention as mentioned above can be carried out not only in the respectively stated combination but also in other combinations or on their own without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for carrying out a cardio-computed tomography (CT) examination of a patient using a CT system having at least two X-ray tubes on a gantry, comprising:
    recording a current electrocardiography (EKG) signal from the patient;
    moving at least one of the patient and the gantry, sequentially, relative to one another in a system axis direction;
    moving the at least two X-ray tubes, arranged at offset angles with respect to one another, on a circular path around the patient for scanning;
    measuring absorption data of the patient; and
    producing CT representations of the patient by selectively using the measured absorption data, wherein
    the moving the at least one of the patient and the gantry sequentially moves at least one of the patient and the gantry relative to one another to at least two positions,
    the moving the at least two X-ray tubes scans the patient using at least two different X-ray spectra at each of the at least two positions,
    the moving the at least two X-ray tubes first scans the patient using a first X-ray spectrum of the at least two different X-ray spectra at two of the at least two X-ray tubes at a first of the at least two positions, until the measuring gathers absorption data for parallel projections over a range of at least 180° from a first heart period,
    the moving the at least two X-ray tubes second scans the patient using a second X-ray spectrum of the at least two different X-ray spectra at the two of the at least two X-ray tubes at the first of the at least two positions, until the measuring gathers absorption data for parallel projections over a range of at least 180° from a second heart period, and
    the moving at least one of the patient and the gantry sequentially moves at least one of the patient and the gantry relative to one another to a second of the at least two positions after the moving the at least two X-ray tubes second scans the patient.

2. The method as claimed in claim 1, wherein the moving at least two X-ray tubes includes three X-ray tubes arranged at angular offsets of 120°.

3. The method as claimed in claim 2, wherein the at least two different X-ray spectra are achieved by variation of the acceleration voltage.

4. The method as claimed in claim 2, wherein the at least two different X-ray spectra are achieved by different radiation filters.

5. The method as claimed in claim 1, wherein the moving at least two X-ray tubes includes two X-ray tubes arranged at angular offsets of 90°.

6. The method as claimed in claim 1, wherein the at least two different X-ray spectra of the radiation are achieved by variation of an acceleration voltage.

7. The method as claimed in claim 1, wherein the at least two different X-ray spectra are achieved by different radiation filters.

8. The method as claimed in claim 1, wherein a tube current is matched such that an applied dose rate remains the same for at least two of the at least two different X-ray spectra.

9. The method as claimed in claim 1, wherein the moving at last one of the patient and the gantry relative to one another is carried out by a movement of a patient couch, on which the patient is located, in the system axis direction.

10. The method as claimed in claim 1, wherein the moving at least one of the patient and the gantry relative to one another is carried out by moving the gantry in the system axis direction.

11. The method as claimed in claim 1, wherein,
    the moving the at least two X-ray tubes changes between one of at least two different X-ray spectra and the moving at least one of the patient and the gantry sequentially moves at least one of the patient and the gantry relative to one another to at least one of the least two positions based on the recording,
    the moving the at least two X-ray tubes first scans the patient during a rest phase of the first heart period and the absorption data is recorded using an associated detector for the two of the at least two X-ray tubes, and
    the moving the at least two X-ray tubes second scans the patient during a rest phase of the second heart period and the absorption data is recorded using the associated detector for the two of the at least two X-ray tubes.

12. The method as claimed in claim 11, wherein, after the rest phase of the second heart period, the moving at least one of the patient and the gantry sequentially moves at least one of the patient and the gantry relative to one another to a subsequent position after the first of the least two positions until a heart region is scanned, where the moving the at least two X-ray tubes carries out the first and second scans at each of the subsequent position.

13. The method as claimed in claim 11, wherein,
the moving the at least two X-ray tubes first scans the patient during a rest phase of a third heart period and the absorption data is recorded using an associated detector for the two of the at least two X-ray tubes, and
the moving the at least two X-ray tubes second scans the patient during a rest phase of a fourth heart period and the absorption data is recorded using the associated detector for the two of the at least two X-ray tubes.

14. The method as claimed in claim 13, wherein, after the rest phase of the fourth heart period, the moving at least one of the patient and the gantry sequentially moves at least one of the patient and the gantry relative to one another to a subsequent position after the first of the least two positions until a heart region is scanned, where the moving the at least two X-ray tubes carries out the first and second scans at each of the subsequent positions.

15. The method as claimed in claim 1, wherein,
the moving the at least two X-ray tubes changes between one of at least two different X-ray spectra and the moving at least one of the patient and the gantry sequentially moves at least one of the patient and the gantry relative to one another to at least one of the least two positions based on the recording,
the moving the at least two X-ray tubes first scans the patient during a rest phase of the first heart period and the absorption data is recorded using an associated detector for the two of the at least two X-ray tubes,
the moving the at least two X-ray tubes second scans the patient during a rest phase of the second heart period and the absorption data is recorded using the associated detector for the two of the at least two X-ray tubes, and
the moving at least one of the patient and the gantry sequentially moves at least one of the patient and the gantry relative to one another to the second of the at least two positions in a third, subsequent heart period.

16. The method as claimed in claim 15, wherein, after a rest phase of the third heart period, the moving at least one of the patient and the gantry sequentially moves at least one of the patient and the gantry relative to one another to a third position after the second of the least two positions until a heart region is scanned, where the moving the at least two X-ray tubes carries out the first and second scans at each of the subsequent positions.

17. The method as claimed in claim 15, wherein,
the moving the at least two X-ray tubes first scans the patient during a rest phase of a third heart period and the absorption data is recorded using an associated detector for the two of the at least two X-ray tubes,
the moving the at least two X-ray tubes second scans the patient during a rest phase of a fourth heart period and the absorption data is recorded using the associated detector for the two of the at least two X-ray tubes, and
the moving at least one of the patient and the gantry sequentially moves at least one of the patient and the gantry relative to one another to a third position after the second of the at least two positions in a fifth, subsequent heart period.

18. The method as claimed in claim 17, wherein, after a rest phase of the fifth heart period, the moving at least one of the patient and the gantry sequentially moves at least one of the patient and the gantry relative to one another to a subsequent position after the third position of the least two positions until a heart region is scanned, where the moving the at least two X-ray tubes carries out the first and second scans at each of the subsequent positions.

19. The method as claimed in claim 1, wherein no dose power is emitted to the patient at least during the moving at least one of the patient and the gantry relative to one another.

20. The method as claimed in claim 1, wherein the measuring takes into account complementary beams for gathering projection data over a projection angle range of at least 180°.

21. The method as claimed in claim 1, wherein the first and second X-ray spectra, do not overlap.

22. A cardio-computed tomography (CT) system for production of CT representations of a patient with a beating heart, comprising:
at least two X-ray tubes, arranged at offset angles with respect to one another, to rotate about a system axis and pass radiation through the patient, with absorption of the radiation being measured;
a control and computation unit including a memory, which contains program code, to evaluate the recorded absorption data during operation and reconstruct the CT representations, wherein the program code is stored in the memory and carries out, when executed on the control and computation unit, the following:
recording a current electrocardiography (EKG) signal from the patient;
moving at least one of the patient and the gantry, sequentially, relative to one another in a system axis direction;
moving the at least two X-ray tubes on a circular path around the patient for scanning;
measuring absorption data of the patient; and
producing CT representations of the patient by selectively using the measured absorption data, wherein
the moving at least one of the patient and the gantry sequentially moves the patient to at least two positions,
the moving the at least two X-ray tubes scans the patient using at least two different X-ray spectra at each of the at least two positions,
the moving the at least two X-ray tubes first scans the patient using a first X-ray spectrum of the at least two different X-ray spectra at two of the at least two X-ray tubes at a first of the at least two positions, until the measuring gathers absorption data for parallel projections over a range of at least 180° from a first heart period,
the moving the at least two X-ray tubes second scans the patient using a second X-ray spectrum of the at least two different X-ray spectra at the two of the at least two X-ray tubes at the first of the at least two positions, until the measuring gathers absorption data for parallel projections over a range of at least 180° from a second heart period, and
the moving at least one of the patient and the gantry sequentially moves at least one of the patient and the gantry relative to one another to a second of the at least two positions after the moving the at least two X-ray tubes second scans the patient.

23. A method for carrying out a cardio-CT examination of a patient using a CT system having at least two X-ray tubes arranged at offset angles with respect to one another on a gantry, comprising:
scanning the patient using two different X-ray spectra at least two relative positions between the patient and the gantry, the patient being first scanned using a first X-ray spectrum by way of at least two X-ray tubes at a first relative position of the at least two relative positions, until the measurement data is gathered for parallel projections over a range of in total at least 180° of projection angles from a determined heart phase, and, without any change in the position of the gantry, the patient is scanned at the first relative position by way of at least two X-ray tubes using at least one second X-ray spectrum, until the measurement data has been gathered for parallel projections over a range of at least 180° of projection angles from a determined heart phase; and moving to a next relative position of the at least two relative positions between the patient and the gantry.

* * * * *